United States Patent
Si et al.

(10) Patent No.: US 12,276,869 B1
(45) Date of Patent: Apr. 15, 2025

(54) WS12-RELEASING CONTACT LENS

(71) Applicant: CooperVision International Limited, Fareham (GB)

(72) Inventors: Erwin Si, Alameda, CA (US); Nancy Keir, Pleasanton, CA (US); Subam Basuthkar Sundar Rao, San Ramon, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 0 days.

(21) Appl. No.: 18/837,611

(22) PCT Filed: Oct. 30, 2023

(86) PCT No.: PCT/GB2023/052823
§ 371 (c)(1),
(2) Date: Aug. 12, 2024

(87) PCT Pub. No.: WO2024/094974
PCT Pub. Date: May 10, 2024

Related U.S. Application Data

(60) Provisional application No. 63/420,738, filed on Oct. 31, 2022.

(51) Int. Cl.
*G02C 7/04* (2006.01)
*A45C 11/00* (2006.01)
*A61F 9/00* (2006.01)

(52) U.S. Cl.
CPC .............. *G02C 7/04* (2013.01); *A45C 11/005* (2013.01); *A61F 9/0017* (2013.01)

(58) Field of Classification Search
CPC ........ G02C 7/04; A45C 11/005; A61F 9/0017
(Continued)

(56) References Cited

U.S. PATENT DOCUMENTS

| 6,867,245 B2 | 3/2005 | Iwata et al. |
| 7,426,993 B2 | 9/2008 | Coldrey et al. |

(Continued)

FOREIGN PATENT DOCUMENTS

| JP | 2011219513 A | 11/2011 |
| JP | 5568174 B1 | 8/2014 |

(Continued)

OTHER PUBLICATIONS

International Search Report and Written Opinion issued in corresponding International Patent Application No. PCT/GB2023/052823 dated Mar. 6, 2024 (12 pages).

(Continued)

*Primary Examiner* — William R Alexander
(74) *Attorney, Agent, or Firm* — Kilyk & Bowersox, P.L.L.C.

(57) ABSTRACT

A WS12-releasing contact lens is described as well as method of manufacturing the same. The WS12-releasing contact lens comprises a polymeric lens body and WS12 releasably adhered to the polymeric lens body. The amount of WS12 releasably adhered to the polymeric lens body provides a basal tear concentration in lens wearers of 2 μg/ml to 8 μg/ml WS12 after 30 minutes of lens wear. The WS12-releasing contact lens can be used to increase contact lens comfort, reduce eye fatigue, reduce sensations of ocular dryness and impart a pleasant, cooling sensation in the lens wearer without causing stinging or burning upon insertion.

14 Claims, 1 Drawing Sheet

(58) Field of Classification Search
USPC .................................................. 351/159.04
See application file for complete search history.

(56) References Cited

U.S. PATENT DOCUMENTS

| | | | |
|---|---|---|---|
| 8,231,218 | B2 | 7/2012 | Hong et al. |
| 8,658,747 | B2 | 2/2014 | Liu et al. |
| 10,028,920 | B2 | 7/2018 | Belmonte Martinez et al. |
| 2011/0313077 | A1 | 12/2011 | Baba et al. |
| 2019/0262290 | A1* | 8/2019 | Horn .................. A61K 47/10 |
| 2020/0009044 | A1 | 1/2020 | Horn |
| 2020/0061002 | A1* | 2/2020 | Horn .................. A61K 31/167 |
| 2020/0397727 | A1* | 12/2020 | Horn .................. A61P 27/04 |
| 2022/0080048 | A1* | 3/2022 | Horn .................. A61K 31/717 |
| 2022/0350163 | A1 | 11/2022 | Si et al. |
| 2023/0350228 | A1 | 11/2023 | Si et al. |

FOREIGN PATENT DOCUMENTS

| | | |
|---|---|---|
| JP | 5764532 B2 | 8/2015 |
| JP | 2022511335 A | 1/2022 |
| JP | 2024544827 A | 12/2024 |
| WO | 2020061249 A2 | 3/2020 |
| WO | 2020178429 A1 | 9/2020 |

OTHER PUBLICATIONS

PCT Demand filed Apr. 23, 2024 in corresponding International Patent Application No. PCT/GB2023/052823 (9 pages).

International Preliminary Report on Patentability issued in corresponding International Patent Application No. PCT/GB2023/052823 dated May 17, 2024 (6 pages).

Office Action issued in corresponding Japanese Patent Application No. 2024-547847 dated Dec. 20, 2024 (4 pages).

* cited by examiner

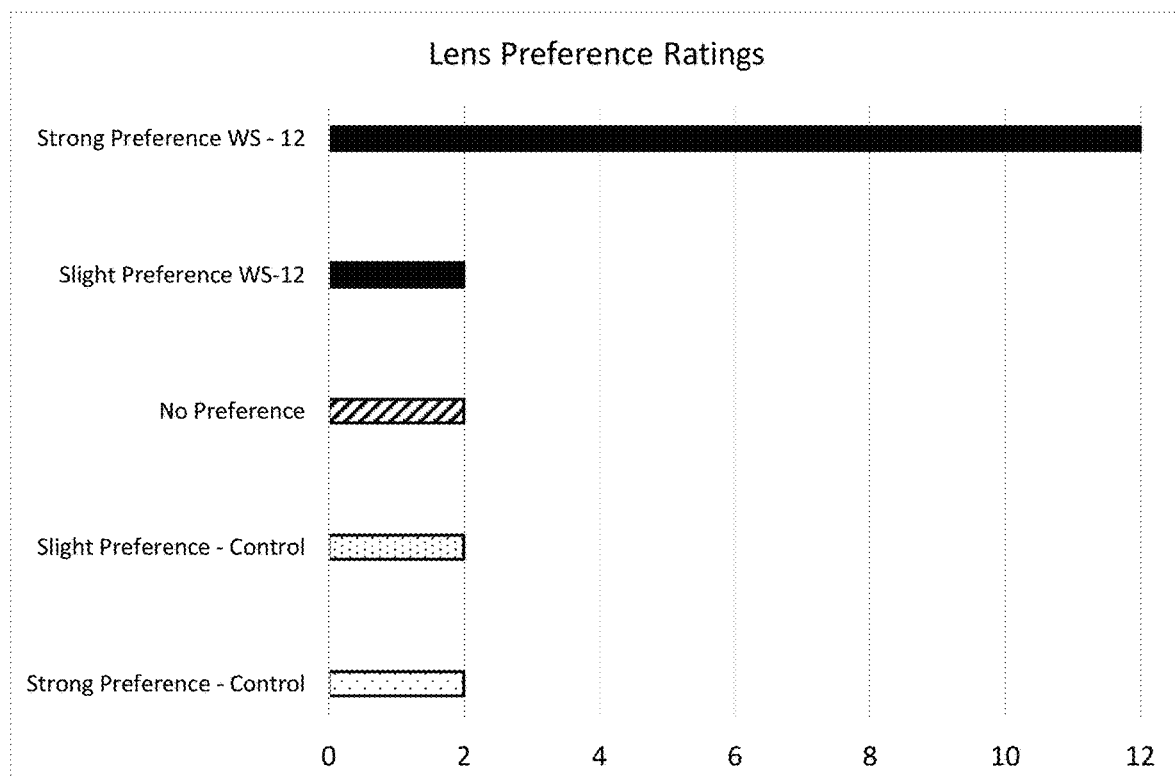

WS12-RELEASING CONTACT LENS

This application is a National Stage Application of PCT/GB2023/052823, filed Oct. 30, 2023, which claims priority to U.S. Patent Application No. 63/420,738, filed Oct. 31, 2022.

FIELD OF THE INVENTION

The field of the invention relates to contact lenses, and particularly, to contact lenses that provide a pleasant cooling sensation when worn.

BACKGROUND

N-(4-Methoxyphenyl)-5-methyl-2-(1-methylethyl)cyclohexanecarboxamide (CAS No. 68489-09-8), known as WS12, is a synthetic menthol derivative. Therapeutic compositions comprising TRPM8 receptor agonists in amounts effective to increase tearing have been proposed for the treatment of dry eye syndrome (Belmonte et al. U.S. Pat. No. 10,028,920).

WS12 can be incorporated into silicone hydrogel contact lenses and withstand autoclave sterilization without degradation or leaching into the packaging solution (U.S. patent application Ser. No. 17/729,008). Such lenses increased tearing, reduced sensations of lens dryness and improved comfortable lens wearing time in symptomatic contact lens wearers. However, for some lens wearers there was a stinging/burning sensation when the contact lens was initially inserted into the eye. This stinging/burning sensation can cause a wearer not to use the contact lens at all even though stinging/burning sensation is temporary.

There is a desire to provide a contact lens that can impart a pleasant, cooling sensation for all contact lens wearers without causing stinging or burning upon insertion.

SUMMARY

A feature of the present invention is to provide a contact lens that can release WS12 during lens wearing without causing insertion stinging or burning.

An additional feature of the present invention is to provide a contact lens that provides a refreshing or cool sensation when the lens is worn.

An additional feature of the present of invention is to provide a contact lens that reduces eye fatigue.

An additional feature of the present invention is to provide a WS12-releasing contact lens that a majority of contact lens wearers find more comfortable to wear than a lens made of the same material but lacking the WS12, regardless of whether they experience symptoms of discomfort or dryness with their habitual contact lenses.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention, in part relates to a hydrogel contact lens containing an amount of WS12 releasably adhered to the lens that enhances the comfort or desirability of the contact lens without increasing tearing in the wearer. In one example, the hydrogel contact lens is a silicone hydrogel contact lens.

In one example, the silicone hydrogel contact lens provides a basal tear concentration of 1.0 ng/ml to 10 ng/ml WS12, or 3 ng/ml to 6 ng/ml WS12 after about 30 minutes of wear.

BRIEF DESCRIPTION OF THE DRAWING

FIG. 1 is a bar chart that shows contact lens wearers preference for either a WS12-releasing contact lens or a control lens after 7 days of lens wear.

DETAILED DESCRIPTION

A clinical study was conducted to determine whether a contact lens that releases a lower amount of WS12 than previously evaluated (as described in U.S. patent application Ser. No. 17/729,008) would show any improvement in comfort ratings without causing any stinging or burning sensation on initial lens insertion. Unexpectedly, the majority of study participants overwhelmingly preferred the low dose WS12-releasing lens over the control lens even though the amount of WS12 used was found to be insufficient to provide an observable increase in the tear volume. It was hypothesized that a contact lens that releases relatively low levels of WS12 can achieve a tear concentration of WS12 that is insufficient to trigger high threshold TRPM8 receptors involved in tearing, yet still provide increased comfort or desirability due to the sensation of cooling. Moreover, the amount of WS12 was insufficient to cause the initial stinging or burning sensations observed with the higher dose lens. Accordingly, hydrogel contact lenses that release low doses of WS12 during wear and their method of manufacture are described herein. The contact lens can be referred to herein as a WS12-releasing contact lens. WS12 is released from the lens during wear in amounts that improve the comfort of the contact lens relative to a control lens, without providing an observable increase in the tear volume of the lens wearers and/or increased insertion stinging relative to a control lens. References herein to a "control lens" refer to a contact lens that contains no WS12 but is otherwise identical to the WS12-releasing lens to which it is being compared.

The WS12-releasing contact lens comprises a polymeric lens body and an amount of WS12 releasably adhered to the polymeric lens body. The amount of WS12 "releasably adhered" to the polymeric lens body refers to the total amount of WS12 that can be extracted from the contact lens by an ethanol (EtOH) extraction method as described in Example 1 below. In one example, the amount of WS12 releasably adhered to the polymeric lens body can be at least about 0.1 µg, 0.2 µg, or 0.3 µg, or 0.4 µg up to about 0.5 µg, or 0.6 µg or 0.7 µg, such as from about 0.3 µg to about 0.6 µg.

In one example, the contact lens releases an amount of WS12 sufficient to provide an average basal tear concentration in lens wearers (n=5) of 1 ng/ml to 10 ng/ml WS12, or 2 ng/ml to 8 ng/ml WS12, or 3 ng/ml to 6 ng/ml WS12 after 30 minutes of lens wear. The concentration of WS12 in contact lens wearers' basal tears can be determined using routine microcapillary tube tear collection methods and HPLC.

In one example, the WS12-releasing contact lens does not increase tearing in the lens wearer relative to a control lens. Increase in tearing is demonstrated if the pre-lens tear meniscus height (TMH) while wearing the WS12-releasing lens is the same as or less than the TMH when a control lens is worn for the same period of time, such as after 1 hour, 2 hours, 4 hours or more. Tear meniscus height may be measured using an OCULUS Keratograph (K5M) or other equivalent method.

As one example, the contact lens is a reaction product of a polymerizable composition for a non-silicone hydrogel. Non-silicone hydrogel contact lenses are typically formed from polymerization of one or more hydrophilic monomers such as 2-hydroxyethyl methacrylate (HEMA) or vinyl alcohol, optionally in combination with other monomers, and contains no siloxane molecule.

As one example, the contact lens comprises a polymeric lens body that is the reaction product of a polymerizable composition comprising at least one siloxane monomer and at least one hydrophilic monomer and/or at least one hydrophilic polymer. Conveniently, as described in more detail below, a cured polymeric lens body for a silicone hydrogel may be extracted in an extraction solvent containing the WS12 which results in the desired amount of WS12 adhering to the polymeric lens body. Alternatively, or additionally, the WS12 may be added to the polymerizable composition. The WS12 may be adhered to the polymeric lens body by hydrophobic interaction, and/or may be physically entrapped by the polymer network of the polymeric lens body.

As used herein, the term "siloxane monomer" refers to any molecule that contains at least one Si—O group and at least one polymerisable functional group. Siloxane monomers used in contact lens compositions are well-known in the art (see, e.g., U.S. Pat. Nos. 8,658,747 and 6,867,245). (All patents and publications mentioned here and throughout are incorporated in their entirety by reference.) In some examples, the polymerisable composition comprises a total amount of siloxane monomer of at least 10 wt. %, 20 wt. %, or 30 wt. % up to about 40 wt. %, 50 wt. %, 60 wt. %, or 70 wt. %. Unless specified otherwise, as used herein, a given weight percentage (wt. %) of a component of the polymerisable composition is relative to the total weight of all polymerisable ingredients and IPN polymers (as described further below) in the polymerisable composition. The weight of the polymerisable composition contributed by components, such as diluents, that do not incorporate into the final contact lens product are not included in the wt. % calculation.

In a specific example, the polymerisable composition comprises a hydrophilic vinyl monomer. As used-herein, a "hydrophilic vinyl monomer" is any siloxane-free (i.e., contains no Si—O groups) hydrophilic monomer having a polymerisable carbon-carbon double bond (i.e., a vinyl group) present in its molecular structure that is not part of an acryl group, where the carbon-carbon double bond of the vinyl group is less reactive than the carbon-carbon double bond present in a polymerisable methacrylate group under free radical polymerization. As used herein, the term "acryl group" refers to the polymerisable group present in acrylate, methacrylates, acrylamides, etc. Thus, while carbon-carbon double bonds are present in acrylate and methacrylate groups, as used herein, such polymerisable groups are not considered to be vinyl groups. Further, as used herein, a monomer is "hydrophilic" if at least 50 grams of the monomer are fully soluble in 1 liter of water at 20° C. (i.e., ~ 5% soluble in water) as determined visibly using a standard shake flask method. In various examples, the hydrophilic vinyl monomer is N-vinyl-N-methylacetamide (VMA), or N-vinyl pyrrolidone (NVP), or 1,4-butanediol vinyl ether (BVE), or ethylene glycol vinyl ether (EGVE), or diethylene glycol vinyl ether (DEGVE), or any combination thereof. In one example, the polymerisable composition comprises at least 10 wt. %, 15 wt. %, 20 wt. %, or 25 wt. % up to about 45 wt. %, 60 wt. %, or 75 wt. % of a hydrophilic vinyl monomer. As used herein, a given weight percentage of a particular class of component (e.g., hydrophilic vinyl monomer, siloxane monomer, or the like) in the polymerisable composition equals the sum of the wt. % of each ingredient in the composition that falls within the class. Thus, for example, a polymerisable composition that comprises 5 wt. % BVE and 25 wt. % NVP and no other hydrophilic vinyl monomer, is said to comprise 30 wt. % hydrophilic vinyl monomer. In one example, the hydrophilic vinyl monomer is a vinyl amide monomer. Exemplary hydrophilic vinyl amide monomers are VMA and NVP. In a specific example, the polymerisable composition comprises at least 25 wt. % of a vinyl amide monomer. In a further specific example, the polymerisable composition comprises from about 25 wt. % up to about 75 wt. % of VMA or NVP, or a combination thereof. Additional hydrophilic monomers that may be included in the polymerisable composition are N,N-dimethylacrylamide (DMA), 2-hydroxyethyl methacrylate (HEMA), ethoxyethyl methacrylamide (EOEMA), ethylene glycol methyl ether methacrylate (EGMA), and combinations thereof.

In addition, or as an alternative to a hydrophilic monomer, the polymerisable composition may comprise a non-polymerisable hydrophilic polymer, which results in a polymeric lens body comprising an interpenetrating polymer network (IPN) with the non-polymerisable hydrophilic polymer interpenetrating the silicone hydrogel polymer matrix. In this example, the non-polymerisable hydrophilic polymer is referred to as an IPN polymer, which acts as an internal wetting agent in the contact lens. In contrast, polymer chains within the silicone hydrogel network that form by polymerization of monomers present in the polymerisable composition are not considered to be IPN polymers. The IPN polymer may be a high molecular weight hydrophilic polymer, for example from about 50,000 to about 500,000 Daltons. In a specific example, the IPN polymer is polyvinylpyrrolidone (PVP). In other examples, the polymerisable composition is substantially free of polyvinyl pyrrolidone or other IPN polymer.

As an option, one or more non-silicon containing hydrophobic monomers can be present as part of the polymerisable composition. A hydrophobic monomer can be understood to be any monomer for which 50 grams of the monomer are not visibly fully soluble in 1 liter of water at 20° C. using a standard shake flask method. Examples of suitable hydrophobic monomers include methyl acrylate, or ethyl acrylate, or propyl acrylate, or isopropyl acrylate, or cyclohexyl acrylate, or 2-ethylhexyl acrylate, or methyl methacrylate (MMA), or ethyl methacrylate, or propylmethacrylate, or butyl acrylate, or 2-hydroxybutyl methacrylate, or vinyl acetate, or vinyl propionate, or vinyl butyrate, or vinyl valerate, styrene, or chloroprene, or vinyl chloride, or vinylidene chloride, or acrylonitrile, or 1-butene, or butadiene, or methacrylonitrile, or vinyltoluene, or vinyl ethyl ether, or perfluorohexylethylthiocarbonylaminoethyl methacrylate, or isobornyl methacrylate (IBM), or trifluoroethyl methacrylate, or hexafluoroisopropyl methacrylate, or tetrafluoropropyl methacrylate, or hexafluorobutyl methacrylate, or any combinations thereof.

The hydrophobic monomer, if used, can be present in the reaction product of the polymerisable composition in amounts of from 1 wt. % to about 30 wt. %, such as from 1 wt. % to 25 wt. %, from 1 wt. % to 20 wt. %, from 1 wt. % to 15 wt. %, from 2 wt. % to 20 wt. %, from 3 wt. % to 20 wt. %, from 5 wt. % to 20 wt. %, from 5 wt. % to 15 wt. %, from 1 wt. % to 10 wt. %, based on the total weight of the polymerisable composition.

The polymerisable composition may additionally comprise at least one cross-linking agent. As used herein, a "cross-linking agent" is a molecule having at least two polymerisable groups. Thus, a cross-linking agent can react with functional groups on two or more polymer chains so as to bridge one polymer to another. The cross-linking agent may comprise an acryl group or a vinyl group, or both an acryl group and a vinyl group. In certain examples, the cross-linking agent is free of siloxane moieties, i.e., it is a non-siloxane cross-linking agent. A variety of cross-linking agents suitable for use in silicone hydrogel polymerisable compositions are known in the field (see, e.g., U.S. Pat. No. 8,231,218, incorporated herein by reference). Examples of suitable cross-linking agents include, without limitation, lower alkylene glycol di(meth)acrylates such as triethylene glycol dimethacrylate, diethylene glycol dimethacrylate, poly(lower alkylene) glycol di(meth)acrylates and lower alkylene di(meth)acrylates; divinyl ethers such as triethylene glycol divinyl ether, diethyleneglycol divinyl ether, 1,4-butanediol divinyl ether and 1,4-cyclohexanedimethanol divinyl ether; divinyl sulfone; di- and trivinylbenzene; trimethylolpropane tri(meth)acrylate; pentaerythritol tetra(meth)acrylate; bisphenol A di(meth)acrylate; phthalate; 1,3-bis(3-methylenebis(meth)acrylamide; triallyl methacryloxypropyl)tetramethyldisiloxane; diallyl phthalate; and combinations thereof.

As will be appreciated by those skilled in the art, the polymerisable composition may comprise additional polymerisable or non-polymerisable ingredients conventionally used in contact lens formulations such as one or more of a polymerization initiator, a UV absorbing agent, a tinting agent, an oxygen scavenger, a chain transfer agent, or the like. In some examples, the polymerisable composition may include an organic diluent in an amount to prevent or minimize phase separation between the hydrophilic and hydrophobic components of the polymerisable composition, so that an optically clear lens is obtained. Diluents commonly used in contact lens formulations include hexanol, ethanol, and/or other primary, secondary or tertiary alcohols. In other examples, the polymerisable composition is free or substantially free (e.g., less than 500 ppm) of an organic diluent. In such examples, the use of siloxane monomers containing hydrophilic moieties such as polyethylene oxide groups, pendant hydroxyl groups, or other hydrophilic groups, may make it unnecessary to include a diluent in the polymerisable composition. Non-limiting examples of these and additional ingredients that may be included in the polymerisable composition are provided in U.S. Pat. No. 8,231,218.

Non-limiting examples of silicone hydrogels that may be used include comfilcon A, fanfilcon A, stenfilcon A, senofilcon A, senofilcon C somofilcon A, narafilcon A, delefilcon A, narafilcon A, lotrafilcon A, lotrafilcon B, balafilcon A, samfilcon A, galyfilcon A, and asmofilcon A.

A specific example of a hydrogel contact lens of the present invention is one that is based on a polymerisable composition comprising from 25 wt. % to 55 wt. % of siloxane monomer(s), from 30 wt. % to 55 wt. % of a vinyl monomer selected from NVP, VMA, or combinations thereof, and optionally from about 1 wt. % to about 20 wt. % of a hydrophilic monomer selected from N,N-dimethylacrylamide (DMA), 2-hydroxyethyl methacrylate (HEMA), ethoxyethyl methacrylamide (EOEMA), or ethylene glycol methyl ether methacrylate (EGMA), or any combination thereof, and optionally from about 1 wt. % to about 20 wt. % of a hydrophobic monomer selected from methyl methacrylate (MMA), isobornyl methacrylate (IBM), or 2-hydroxybutyl methacrylate (HOB) or any combination thereof. Silicone hydrogel materials made from this specific embodiment of polymerisable composition include stenfilcon A, comfilcon A, somofilcon A, fanfilcon A, and enfilcon A. In a further example, the above-described polymerizable composition comprises the siloxane monomers of stenfilcon A, specifically a first siloxane monomer having the structure represented by Formula (I),

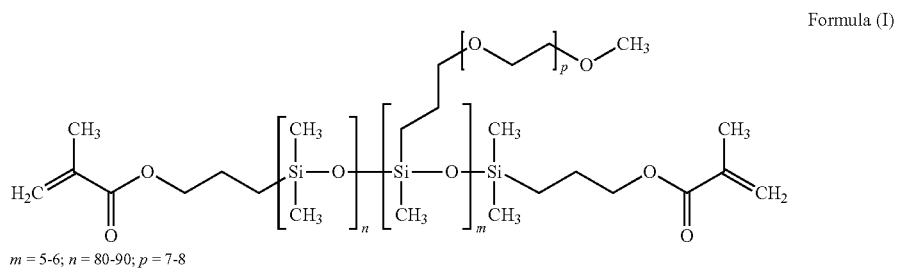

Formula (I)

and a second siloxane monomer having the structure represented by Formula (II),

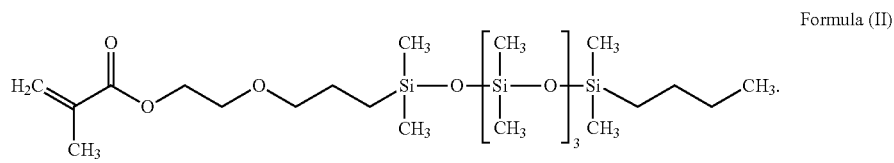

Formula (II)

Conventional methods can be used to manufacture the contact lens of the invention. As an example, a polymerisable composition for a hydrogel composition is dispensed into a female mold member having a concave surface that defines the front surface of the contact lens. A male mold member having a convex surface that defines the back surface of the contact lens, i.e., the cornea-contacting surface, is combined with the female mold member to form a contact lens mold assembly that is subjected to curing conditions, such as UV or thermal curing conditions, under which the curable composition is formed into a polymeric lens body. The female and male mold members can be non-polar molds or polar molds. The mold assembly is disassembled (i.e., demolded) and the polymeric lens body is removed from the mold and unreacted components are extracted from the lens body using an organic solvent.

Conveniently, the WS12 may be loaded into the polymeric lens during the extraction step. Generally, after curing, the polymeric lens body is swelled in an extraction solvent that contains the WS12. When the extracted polymeric lens body is subsequently placed in a hydration solution, such as deionized water, the extraction solvent is removed, and the WS12 remains adhered to the polymeric lens body.

As an example, the extraction and hydration process can involve at least one extraction step in denatured ethanol (EtOH) followed by an extraction step comprising a mixture of EtOH and water, such as from about 10% to 95% EtOH in water, for example from about 30% to 80% EtOH in water, followed by at least one hydration step in deionized water, and wherein each extraction and hydration step can last from about 15 minutes to about 3 hours at a temperature of from about 20° C. and to about 30°. Any extraction solvent can be used as an uploading solution for the WS12. In one example, the concentration of WS12 in the extraction solvent is from about 1.0 μg/ml to about 4.0 μg/ml (i.e. 1 ppm to about 4 ppm). In one example, the initial extraction solvent is EtOH and the second extraction solvent comprises a mixture of from 30% to 80% EtOH in water and from 1 ppm to 4 ppm WS12.

As part of the present invention, the contact lens can be sealed in a contact lens package. The packaging solution sealed within the contact lens package may be any conventional contact-lens compatible solution. In one example, the packaging solution comprises, consists, or consists essentially, of an aqueous solution of a buffer, and/or a tonicity agent. In another example, the packaging solution contains additional agents such as one or more additional antimicrobial agents, and/or a comfort agent, and/or a hydrophilic polymer, and/or a surfactant and/or other beneficial agent. In some examples, the packaging solution may comprise polysaccharides (e.g., hyaluronic acid, hydroxypropyl methylcellulose, hydroxypropyl cellulose, hydroxyethyl cellulose, etc.) or other high molecular weight polymers, such as polyvinyl pyrrolidone, which are commonly used as comfort polymers or thickening agents in ophthalmic solutions and contact lens packaging solutions. In other examples, the packaging solution may comprise an ophthalmic drug. The packaging solution can have a pH in the range of about 6.8 or 7.0 up to about 7.8 or 8.0. In one example, the packaging solution comprises phosphate buffer or borate buffer. In another example, the packaging solution comprises a tonicity agent selected from sodium chloride or sorbitol in an amount to maintain osmolality in the range of about 200 to 400 mOsm/kg, and typically from about 270 mOsm/kg up to about 310 mOsm/kg.

With respect to the contact lens package, this package can include or comprise a plastic base member comprising a cavity configured to retain the contact lens and packaging solution and a flange region extending outwardly around the cavity. A removable foil is attached to the flange region to provide a liquid-tight seal. The removable foil may be sealed by any conventional means such as heat sealing or gluing. Such contact lens packages, which are commonly referred to as "blister packs", are well-known in the art (see e.g., U.S. Pat. No. 7,426,993). The sealed package may be sterilized by sterilizing amounts of radiation, including heat or steam, such as by autoclaving, or by gamma radiation, e-beam radiation, ultraviolet radiation, etc. In a specific example, the packaged contact lens is sterilized by autoclaving.

The final product can be a sterile, packaged contact lens (e.g., silicone hydrogel contact lens) having ophthalmically-acceptable surface wettability.

In some examples, the WS12, once adhered to the polymeric lens body is stable and does not substantially release from the polymeric lens body or degrade during autoclaving of the sealed contact lens package that contains the unworn hydrogel contact lens in a packaging solution, or during storage in its packaging solution, but does release during lens wear. Thus, the packaging solution that the contact lens is immersed in, before autoclaving, or immediately after autoclaving, or after 1 day thereafter, or after 30 days thereafter, or after 60 days thereafter, or after 120 days thereafter has a concentration of WS12 that is less than the level of detection as determined by HPLC.

In one example, the contact lens is sealed in a blister package as described above, and the blister package is further packaged in secondary packaging that contains a plurality of blister packages, such as at least 7, 14, 30, 60, or 90 blister packages, wherein every blister package with the secondary packaging contains a contact lens comprising an amount of WS12 that is the same as every other contact lens contained by the secondary packaging. As one example every contact lens contained by the secondary packaging comprises a polymeric lens body comprising from 0.2 μg to 0.7 μg, or from 0.3 μg to 0.6 μg, WS12, releasably adhered to the polymeric lens body, and wherein each of the contact lenses contains the same amount of WS12 (e.g. every contact lens contains 0.4 μg WS12 releasably adhered to the polymeric lens body).

The WS12-releasing hydrogel contact lens described herein can be used to increase contact lens comfort in a contact lens wearer.

The WS12-releasing hydrogel contact lens described herein can be used to reduce or prevent eye tiredness in a contact lens wearer. In one example the eye tiredness is associated with use of digital devices, also referred to as "digital eye strain", "digital eye fatigue", or "computer vision syndrome".

The WS12-releasing hydrogel contact lens described herein can be used to reduce sensations of ocular dryness in a contact lens wearer.

The WS12-releasing hydrogel contact lens described herein can be used to impart a pleasant, cooling sensation in a contact lens wearer without causing stinging or burning upon insertion The following Examples illustrate certain aspects and advantages of the present invention, which should be understood not to be limited thereby.

Example 1. Preparation of WS12-Releasing Contact Lens

Silicone hydrogel contact lenses were prepared by curing the formulation for stenfilcon A in contact lens molds. The cured stenfilcon A was removed from the molds and extracted by immersing them for 215 minutes in ethanol (EtOH) containing WS12 (Tocris Bioscience) in the loading concentrations shown in Table I. The lenses were removed from the EtOH and washed in DI water for approximately 6 minutes, followed by two exchanges of DI water for approximately 30 minutes each. The lenses were transferred to 6 mL glass vials containing 3 mL phosphate buffered saline at pH 7.5 (0.78 wt. % NaCl, 0.05 wt. % sodium phosphate monobasic, and 0.36 wt. % sodium phosphate dibasic), referred to herein as PBS. The vials were sealed and autoclaved.

Each autoclaved lens was transferred to a vial containing 3 ml EtOH and stored overnight on a 150 rpm shaker at room temperature to extract WS12 from the lens. The EtOH extracts and the PBS in which the lenses were autoclaved were submitted for analysis by HPLC (detection wavelength=250 nm) against calibration standards to determine the average amount of WS12 loaded into each (n=5) and whether the WS12 leaches from the lens during autoclave. Results are shown in Table 1.

TABLE 1

| Lens ID | WS12 loading concentration | Ave. WS12/lens | WS12 concentration in PBS packaging solution |
|---|---|---|---|
| A | 5 µg/mL | 0.42 µg | Not detected |
| B | 15 µg/mL | 1.28 µg | Not detected |
| C | 50 µg/mL | 4.30 µg | 0.05 µg/mL |

Example 2. 1-Week Cross-Over Clinical Study of WS12-Releasing Contact Lenses

Twenty participants were enrolled in a 1-week, bilateral, randomized, crossover double-masked (investigator and participant) study. The participants were considered symptomatic lens wearers if two criterion were met: 1) they reported that their total daily contact lens wear time (of their habitual lenses) less their comfortable daily contact lens wear time was 3 hours or more, and 2) they were classified as symptomatic using the classification system outlined in Table 2, which is adapted from the classification proposed by Young et al. (Characterizing contact lens-related dryness symptoms in a cross-section of UK soft lens wearers. Contact Lens & Anterior Eye 34 (2011) 64-70).

TABLE 2

| | | Frequency of contact lens dryness/discomfort | | | | |
|---|---|---|---|---|---|---|
| | | Never | Rarely | Sometimes | Frequently | Constantly |
| Intensity of contact lens dryness discomfort | Never have it 0 | A | A | A | A | A |
| | Not at all intense 1 | A | A | A | A | A |
| | 2 | A | A | S | S | S |
| | 3 | A | A | S | S | S |
| | 4 | A | A | S | S | S |
| | Very intense 5 | A | A | S | S | S |

Ten of the subjects were classified as symptomatic contact lens wearers, reporting a rating of 2 or more out of 5 for Intensity of contact lens dryness/discomfort and "sometimes, frequently or constantly" for Frequency of contact lens dryness/discomfort. The remaining 10 participants were classified as asymptomatic contact lens wearers, reporting a rating of 0 or 1 out of 5 for Intensity of contact lens dryness/discomfort and "rarely or never" for Frequency of contact lens dryness/discomfort.

The WS12-releasing lenses comprised stenfilcon A contact containing approximately 0.42 µg WS12/lens. MyDay® brand contact lenses were used as the control lens. The participants wore the study lenses for at least 8 hours per day removing them each night, each for 1-week. After a washout period of 2-4 days during which subjects wore their habitual lenses, the second lens type from the randomization order was worn for 1-week.

Results:

The WS12-releasing lens exhibited significantly better comfort at insertion on the lens dispense visit and at the one-week follow-up visit.

Overall, the WS12-releasing lens felt cooler than the control lens at insertion, with differences statistically significant at the one-week follow-up visit only.

Pleasantness ratings were overall similar between the WS12-releasing and control lenses at all timepoints.

Insertion stinging/burning sensation was overall low and similar between the WS12-releasing and control lenses.

The pre-lens tear meniscus height, measured by keratography, was similar between both the WS12-releasing and control lenses indicating that tear production was not increased by the WS12-releasing lenses.

Participants reported significantly less eye tiredness at lens removal on day 5 with the WS12-releasing lens.

Subjective ratings for dryness were significantly less for the WS12-releasing lens.

Seventy percent of the subjects (14/20) preferred the WS12-releasing lens at end of the day on Day 5 and at the final study visit. The majority of subjects reported a strong preference towards the WS12-releasing lens. The overall lens preference ratings are shown in FIG. 1.

The disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

References herein to "an example" or "a specific example" or "an aspect" or "an embodiment" or similar phrase, are intended to introduce a feature or features of the WS12-releasing hydrogel contact lens or components thereof, the sealed contact lens package or components thereof, or method of manufacturing the WS12-releasing hydrogel contact lens (depending on context) that can be combined with any combination of previously-described or subsequently-described examples, aspects, embodiments (i.e. features), unless a particular combination of features is mutually exclusive, or if context indicates otherwise. Further, as used in this specification, the singular forms "a," "an," and "the" include plural referents (e.g. at least one or more) unless the context clearly dictates otherwise. Thus, for example, reference to a "contact lens" includes a single lens as well as two or more of the same or different lenses.

The entire contents of all cited references in this disclosure, to the extent that they are not inconsistent with the present disclosure, are incorporated herein by reference.

The present invention can include any combination of the various features or embodiments described above and/or in the claims below as set forth in sentences and/or paragraphs. Any combination of disclosed features herein is considered part of the present invention and no limitation is intended with respect to combinable features.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An unworn sterile silicone hydrogel contact lens immersed in a packaging solution and sealed in a package, said contact lens comprising:
   (a) a polymeric lens body; and
   (b) an amount of WS12 releasably adhered to the polymeric lens body, wherein, the amount of WS12 releasably adhered to the polymeric lens body provides a basal tear concentration in lens wearers of 2 ng/ml to 8 ng/ml WS12 after 30 minutes of lens wear.

2. The contact lens of claim 1, wherein the basal tear concentration of WS12 after 30 minutes of lens wear is 3 ng/ml to 6 ng/ml.

3. The contact lens of claim 1, wherein the amount of WS12 releasably adhered to the polymeric lens body is from 0.2 µg to 0.7 µg.

4. The contact lens of claim 1, wherein the amount of WS12 releasably adhered to the polymeric lens body is from about 0.3 µg to about 0.6 µg.

5. The contact lens of claim 1 that does not increase tear meniscus height compared to a control lens.

6. The contact lens of claim 1, wherein the package is autoclaved.

7. The contact lens of claim 1, wherein any WS12 in the packaging solution is less than the level of detection as determined by HPLC.

8. The contact lens of claim 1, wherein the package is a blister package comprising:
   (a) a plastic base member comprising a cavity configured to retain the contact lens and packaging solution;
   (b) a flange region extending outwardly around the cavity; and
   (c) a removable foil attached to the flange region.

9. The contact lens of claim 8 further comprising secondary packaging, wherein the secondary packaging comprises a plurality of blister packages, and wherein every blister package within the secondary packaging contains a contact lens comprising an amount of WS12 that is the same as every other contact lens contained by the secondary packaging.

10. The contact lens of claim 9, wherein the secondary packaging contains at least 7 blister packages.

11. Use of the contact lens of claim 1 to increase contact lens comfort in a contact lens wearer.

12. Use of the contact lens of claim 1 to reduce eye tiredness in a contact lens wearer.

13. Use of the contact lens of claim 1 to reduce sensations of ocular dryness in a contact lens wearer.

14. Use of the contact lens of claim 1 to impart a pleasant, cooling sensation in a contact lens wearer without causing stinging or burning upon insertion.

\* \* \* \* \*